United States Patent [19]

Martin et al.

[11] Patent Number: 4,787,847
[45] Date of Patent: Nov. 29, 1988

[54] DENTAL HYGIENE DEVICE

[75] Inventors: Roy W. Martin; L. David Engel, both of King County, Wash.; Joseph M. Miller, Washtenaw, Mich.

[73] Assignee: The University of Washington, Seattle, Wash.

[21] Appl. No.: 716,371

[22] Filed: Mar. 26, 1985

[51] Int. Cl.⁴ ............................................. A61C 3/03
[52] U.S. Cl. ................................... 433/119; 433/216; 15/22 A; 128/62 A
[58] Field of Search ............ 433/119, 216; 128/24 A, 128/62 A; 15/22 R, 22 A, 167 R

[56] References Cited

U.S. PATENT DOCUMENTS

| Re. 28,752 | 3/1976 | Balamuth et al. | 433/119 |
|---|---|---|---|
| 3,335,443 | 8/1967 | Parisi et al. | 433/119 |
| 3,488,788 | 1/1970 | Robinson | 15/22 R |
| 3,547,110 | 12/1970 | Balamuth | 128/62 A |
| 3,636,947 | 1/1972 | Balamuth | 128/24 A |
| 3,651,576 | 3/1972 | Massa | 433/119 |
| 3,703,037 | 11/1972 | Robinson | 433/86 |
| 3,760,799 | 9/1973 | Crowson | 128/62 A |
| 3,809,977 | 5/1974 | Balamuth et al. | 433/119 |
| 3,847,662 | 11/1974 | Massa | 128/24 A |
| 3,924,335 | 12/1975 | Balamuth et al. | 433/119 |
| 4,144,646 | 3/1979 | Takemoto et al. | 433/119 |
| 4,176,454 | 12/1979 | Hatter et al. | 433/119 |
| 4,192,035 | 3/1980 | Kuris | 15/22 R |
| 4,236,510 | 12/1980 | Hatter et al. | 128/24 A |
| 4,333,197 | 6/1982 | Kuris | 433/119 |

Primary Examiner—John J. Wilson
Attorney, Agent, or Firm—Seed and Berry

[57] ABSTRACT

A method and apparatus for demobilizing the motile subgingival bacteria and for removing soft plaque from the teeth on a substantially daily basis as a means to prevent, treat and/or limit periodontal diseases. A piezoelectric multimorph transducer is used to generate low-energy vibrations, these vibrations are applied to the teeth and gingival fluids to cause mild cavitation within the fluid to remove subgingival plaque and to demobilize motile bacteria. An electronic circuit for driving the transducer at its resonant frequency or multiples thereof and for electrically isolating the user are included.

19 Claims, 3 Drawing Sheets

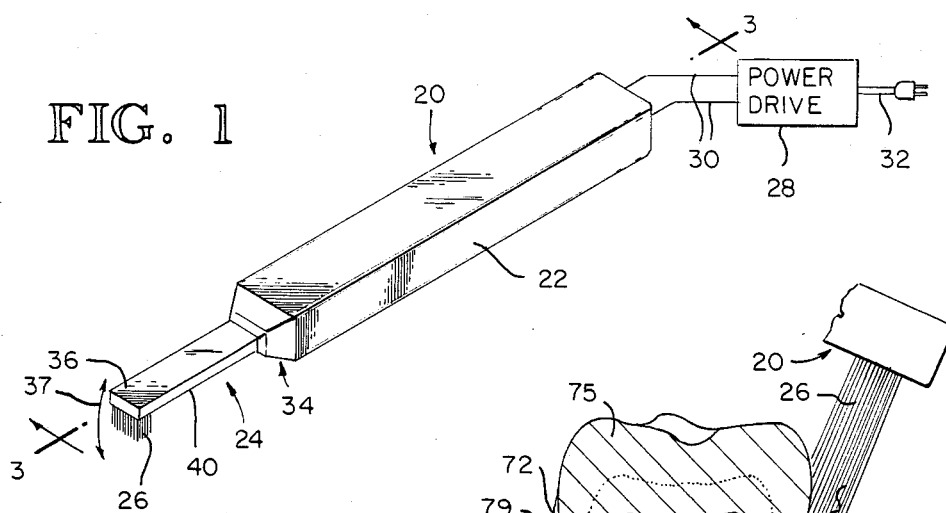
FIG. 1
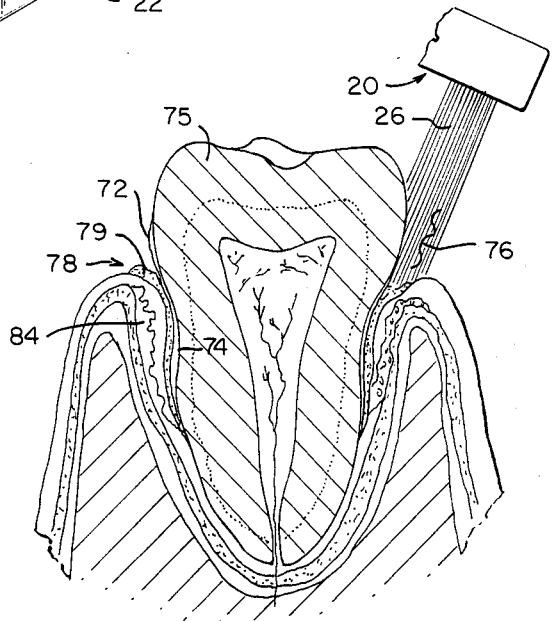
FIG. 2
FIG. 3
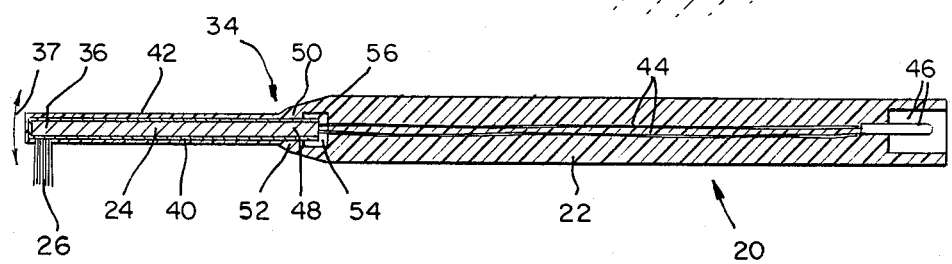
FIG. 4
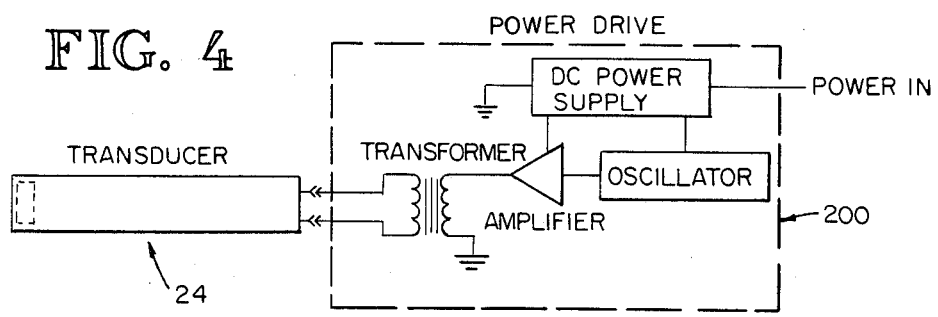

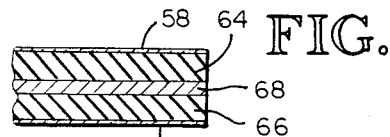
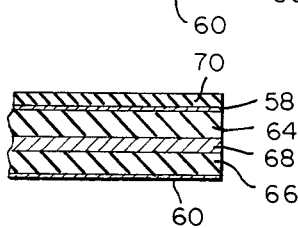
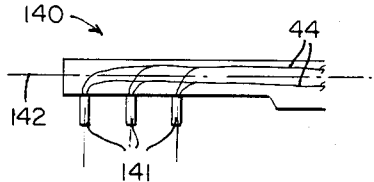
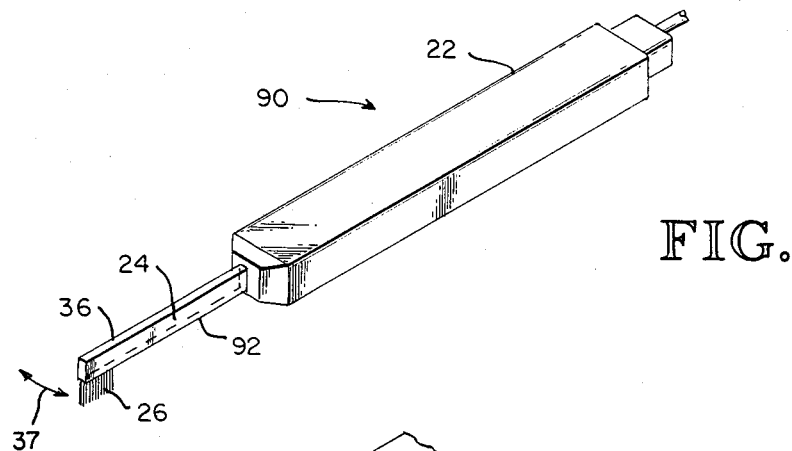
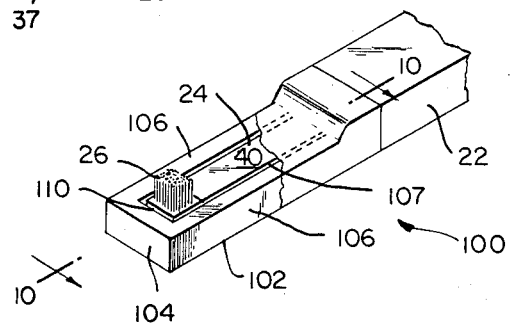
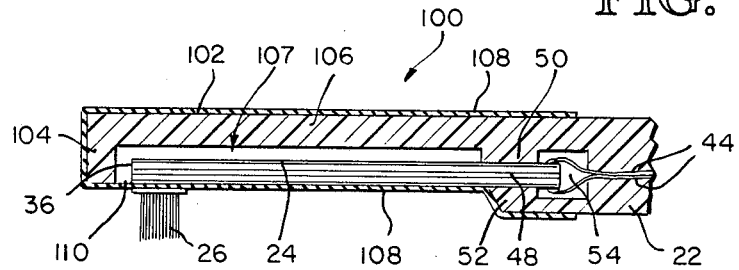

DENTAL HYGIENE DEVICE

TECHNICAL FIELD

This invention relates to dental hygiene devices. Specifically, the invention relates to a method and apparatus for cleaning soft, non-calcified bacterial plaque from the teeth and gingival areas at home on a substantially daily basis.

BACKGROUND ART

The presence of periodontal diseases in a significant portion of the population has indicated a need for methods and devices to prevent the formation of bacterial plaque colonies in the periodontal areas. It is well established that plaque bacteria are the primary cause of periodontal diseases. Various devices have been made available to professional dentists and periodontists to periodically remove tartar or calculus (largely calcified plaque deposits) from the teeth at regular intervals. In addition to passive instruments for scraping this calcified material from the roots of the teeth, devices employing sonic energy at high levels to remove calculus are also available. These devices typically employ high energy levels at ultrasonic frequencies to impart substantial energy to the hardened plaque (calculus) to disrupt it. Thus, these devices serve to destroy calcified plaque colonies after they have formed rigid structures.

These devices are unsuitable for daily home use due to the high energy levels which are transferred to the teeth. In the hands of a non-professional, such devices can cause severe damage to the teeth and surrounding soft tissues. While applying high-energy levels to the teeth and subgingival areas at relatively extended intervals between applications destroys existing rigid calcified structures, it does not prevent the formation of these calcified structures. It is known that bacterial plaque, over time, undergoes a multilayer building process, involving the sequential addition of more and more different species of organisms to the plaque mass. It is the later stages of plaque development, and the later species of bacteria, that are believed to be the most important in the etiology of periodontal diseases. Certain gram-negative bacteria and spirochetes are believed likely to be of greatest importance. Thus, the presently available devices are not suitable for daily home use and do not disrupt the multilayer building process in the formation stage to prevent periodontal diseases.

Furthermore, these devices cannot prevent periodontal disease even if used on a regular basis. This is because the energy levels associated with these devices would be disruptive to the tooth and gum structure if so used in an attempt to destroy plaque colonies before they mature to the complex later stages and before the process of calcification has occurred.

DISCLOSURE OF INVENTION

The present invention allows the daily application of sonic energy to the teeth and subgingival areas so that plaque may be disrupted and destroyed before maturation to the complex pathologic state and before calcification has occurred. The normal flushing action of the mouth and gingival crevices will remove the destroyed or demobilized bacteria from the gingival areas, thus effectively preventing, or stopping, periodontal diseases and substantially reducing the need for scaling of hard calculus by dental professionals.

The invention achieves this objective by utilizing a piezoelectric, multimorph transducer which is caused to vibrate at its resonant frequency or multiples thereof. These frequencies are in the subaudio range to provide for the disruption and removal of plaque and for interrupting and limiting the process of plaque maturation and development at energy levels which are harmless to the surrounding soft tissues. Thus the device may be used at home on a substantially daily basis to prevent the development of pathogenic bacterial flora and the formation of hardened plaque (calculus) which, when formed, requires removal by professional dental personnel using high energy devices or scaling.

The transducer is mounted on a non-conducting handle in a cantilevered fashion. That is, one end of the transducer is firmly attached to the handle while the unattached end is free to vibrate. Thus the transducer forms an oscillator having maximum displacement at the free end of the transducer. In one embodiment, the transducer is driven by appropriate means at the transducer's resonant frequency. The transducer has a substantially rectangular shape, wherein the length of the transducer is substantially greater than the width and the thickness of the transducer is substantially less than the width. Thus the resonant frequency of the transducer is substantially determined by the geometry thereof.

An applicator member (in one embodiment, a brush) is fixed to the free end of the transducer and extends from the transducer to scrub exposed surfaces of the teeth and to transmit the vibrations of the transducer to the subgingival areas. Mild cavitation is caused within the subgingival fluids and has been found to disrupt adherent plaque colonies and to demobilize motile bacteria without harming the surrounding soft tissue.

Means for generating a high-voltage, sonic frequency signal for transmission to the transducer are included to drive the transducer at its resonant frequency or at multiples of the resonant frequency.

In one embodiment, the transducer is electrically insulated by a flexible covering, protecting the user from electrical shock. An isolated power drive unit further isolates the user from low-frequency, high-current signals which are known to cause physiological stimulation. The power drive unit is constructed so that the driving signal is embedded in an amplitude-modulated, high-frequency carrier wave, so that if a short occurs or if there are imperfections in the isolated supply, allowing some current leakage between the user and the power drive unit, only high-frequency power will be transferred to the user, which does not induce physiological stimulation.

In another embodiment, the transducer is surrounded by a hood at least longitudinally coextensive with the transducer and spaced sufficiently apart from the transducer to allow the transducer to vibrate freely within the hood. The hood has an open side to allow vibrations to be transferred from the transducer in the direction of the open side. Thus, when the device is used in the mouth, vibrations from the transducer will only be transferred in one direction, shielding the transducer from vibration dampening contact with the cheek and other oral tissues. A flexible protective covering or fluid-exclusion sheath surrounds the hood and the exposed surface of the transducer to prevent fluid from entering the space between the transducer and the hood. The sheath is bonded to the transducer along the exposed surface of the transducer. An applicator is attached to the outward side of the sheath, proximal to the free end of the transducer, and extends therefrom to transfer the vibrations from the transducer to the teeth and gingival areas.

The transducer itself has at least two layers of piezoelectric material having opposite polarity, bonded to an intermediate conducting layer. Means for applying an electrical signal to the unbonded surfaces of the piezoelectric layers are provided so that the transducer may bend in response to an electrical signal.

The applicator serves to couple the vibrations of the transducer to the gingival and subgingival fluid so that mild cavitation can be caused within the fluid to destroy and demobilize motile plaque bacteria. The applicator can be a brush having a plurality of bristles sized to enter the subgingival crevices and pockets to contact the fluid therein. The shape of the bristles can be varied to provide penetration into the gingival crevices and pockets. In one embodiment, the applicator is a second piezoelectric, multimorph transducer attached to and extending from the surface of the first transducer so that vibration will be produced in two directions. Furthermore, the transducer applicator may be attached to different surfaces of the first transducer so that in different embodiments, the transducer applicators will vibrate orthogonally compared to each other.

In another embodiment, one or more transducers are used. The transducers are mounted perpendicularly to the longitudinal axis of the handle, and serve as the applicators. In this embodiment the applicators are constructed from a resilient polymer material exhibiting piezoelectric characteristics. The transducer applicators may have various pointed or reduced end shapes for coupling sonic energy to the teeth and subgingival fluid.

In a further embodiment, the transducer is removably attached to the handle, providing a dental hygiene device having a replaceable transducer.

BRIEF DESCRIPTION OF THE DRAWINGS

FIG. 1 is an isometric view of a dental hygiene device of the present invention and a power drive unit therefor.

FIG. 2 is a diagram of the device of FIG. 1 shown in use.

FIG. 3 is an enlarged scale, sectional side elevational view taken substantially along the line 3—3 of FIG. 1.

FIG. 4 is a schematic drawing and circuit diagram of the device and power drive unit of FIG. 1.

FIG. 5 is a fragmentary side elevational view of a piezoelectric biomorph transducer used in the device of FIG. 1.

FIG. 6 is a fragmentary side elevational view of an alternative piezoelectric bimorph transducer including a spring.

FIG. 7 is a fragmentary sectional side view of an alternative embodiment of the invention having a plurality of transducers extending perpendicularly from the longitudinal axis of the handle.

FIG. 8 is an isometric view of another alternative embodiment of the invention having an applicator extending perpendicularly to the direction of vibration.

FIG. 9 is a fragmentary isometric view of yet another alternative embodiment of the invention having a transducer with a hood.

FIG. 10 is an enlarged scale, fragmentary sectional side elevational view taken substantially along the line 10—10 of FIG. 9 with the addition of a sheath around the hood.

BEST MODE FOR CARRYING OUT THE INVENTION

Figure 11:
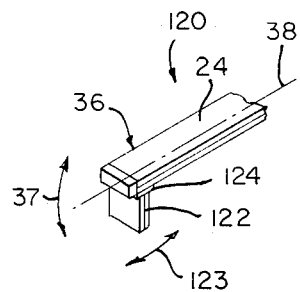
FIG. 11 is a fragmentary isometric view of another alternative embodiment of the invention providing dual-motion.

Referring now in detail to the drawings, the reference numerals herein refer to like numbered parts in the drawings.

A dental hygiene device 20, in accordance with the present invention, is shown in FIG. 1. The device 20 has a handle 22, a transducer 24, and an applicator 26. The device 20 is energized by a low-frequency, high-voltage, low-power driving signal from an isolated power drive unit 28. The signal is transferred to the device 20 through low-frequency wires 30. The power drive unit is energized by conventional house current through an alternating current power line 32.

In one embodiment, as seen in FIGS. 1 and 3, the transducer 24 has a length substantially greater than its width and a thickness substantially less than its width. The transducer extends longitudinally from the handle 22. The transducer is mounted in a cantilevered fashion in the handle, that is, a first attached end 34 of the transducer projects within and is rigidly attached to the handle 22. A second, free end 36 of the transducer is free to vibrate with displacement in a direction indicated by double headed arrow 37, generally perpendicular to the longitudinal axis of the transducer.

The transducer, constructed in this manner, becomes a resonator such that the maximum displacement of the free end will occur at the resonant frequency for the transducer; the resonant frequency being defined substantially by the length and mass of the transducer. Thus, the free end 36 of the transducer will undergo maximum displacement when the transducer is driven at its resonant frequency. The fundamental mode of vibration for the transducer is defined by: $fo = C/L^2 \ 10^6$ Hz, where L is equal to the free length (the distance which the transducer extends from the handle) of the transducer, and where C is a constant primarily related to the mass and stiffness of the transducer. Other modes, or harmonics, of the fundamental frequency can be applied to the transducer, resulting in a smaller displacement of the free end of the transducer.

The applicator 26 extends transversely from the longitudinal axis of the transducer 24 and is firmly attached to a face 40 of the transducer near its free end 36. The applicator can be a brush having a plurality of bristles sized to enter subgingival crevices and pockets to transmit the vibrations from the free end of the transducer to the fluids within these areas.

The dimensions and mass of the transducer are selected so that the resonant frequency of the transducer 24 will be within the range of about 200 to 500 Hertz, with an optimum frequency of about 350 Hertz. It has been found that at this frequency, mild cavitation occurs within the subgingival fluid sufficient to disrupt and remove plaque and to demobilize motile rods and spirochetes without damaging the surrounding soft tissues. It is highly preferred that the device be used daily to destroy and disrupt plaque colonies while still soft, allowing the normal flushing action of the mouth and gingival crevice fluids to remove the destroyed and disrupted plaque colonies. Daily use will also prevent the formation of hard, calcified plaque (calculus) which can only be removed by dental professionals. It has been shown that application of this device to human plaque for about five seconds results in dispersion of the plaque and the bacteria responsible for plaque formation with demobilization of the flagellated and spirochete bacteria, without damage to human epithelial and white blood cells.

The device 20 is shown in FIG. 3 with an electrically non-conducting, elastic covering 42 which covers the exposed surfaces of the transducer 24. The applicator 26 is attached to the elastic covering at the free end 36 of the transducer. A low-frequency driving signal is transmitted to the transducer by internal wires 44 from a pair of contacts 46 which are adapted to engage the low-frequency wires 30. The wires 44 extend the length of the handle within the handle.

It is highly preferred to clamp the transducer 24 to the handle 22 at a nodal point 48 near the attached end 34 of the transducer. The attached end is clamped between an upper restraining handle portion 50 and a lower restraining handle portion 52. A cavity 54 is provided within the restraining handle portions so that a second vibrating end portion 56 of the transducer inward of the nodal point 48, may vibrate freely within the handle. Mounting the transducer in this fashion prevents transmission of any vibration from the transducer to the handle, preventing unpleasant vibrations in the handle. The transducer may be made selectively detachable from the handle.

A detailed view of the transducer 24 is provided in FIG. 5. The transducer has an upper conducting plate 58 and a lower conducting plate 60 for introducing an alternating electric field across an upper piezoelectric plate 64 and a lower piezoelectric plate 66 positioned therebetween. The upper and lower conducting plates may be applied to the piezoelectric plates by any appropriate means including vacuum deposition. In one configuration, the upper and lower piezoelectric plates have opposing polarities. Thus, when an electric field is applied across the conducting plates, one piezoelectric plate will tend to lengthen while the other will tend to shorten. The result is a bending or concavity produced in the transducer.

When the polarity of the electric field across the upper and lower conducting plates is reversed, the transducer will bend in the opposite direction. Thus, application of an alternating electric field across the transducer will cause the transducer to vibrate. Mounting the transducer in the cantilevered fashion as described will cause the transducer to vibrate as a resonator when the alternating electric field is applied to the transducer at the correct frequency, providing for maximum deflection of the applicator 26 in a direction perpendicular to the longitudinal axis of the transducer.

An intermediate conducting layer 68 is provided between the upper piezoelectric plate 64 and the lower piezoelectric plate 66. The conducting layer serves to provide electrical continuity between the piezoelectric plates and to bond the piezoelectric plates together. In FIG. 6, a leaf spring 70 has been bonded to the exposed surface of the upper conducting plate 58 to alter the natural resonant frequency of the transducer.

In another configuration, the polarities of piezoelectric plates 66 and 64 are not opposed but are in the same direction. However, the upper conducting plate 58 and the lower conducting plate 60 are electrically connected together and to one side of the drive circuit. The other side of the drive circuit is connected to the intermediate conducting layer 68. This is the preferred configuration since it requires half the voltage to produce the same vibration and force described in the earlier configuration.

More than two layers of piezoelectric material can be used in the transducer. Numerous other combinations of polarity directions and interconnections can be implemented in order to enhance the mechanical driving response of the transducer and to minimize the required excitation or drive voltage.

FIG. 2 illustrates the dental hygiene device 20 in use. It is highly desired to remove both adherent supragingival plaque 72 and adherent subgingival plaque 74 from the tooth 75. The device 20 delivers subsonic energy, indicated schematically by the line 76, which is generated by the cantilevered transducer 24, through the applicator 26 to the tooth 75 and periodontal pocket 78. Direct scrubbing action against the tooth 75 can be used to remove the supragingival plaque 72 while the gingival fluid 79 couples the sonic energy to the periodontal pocket 78. By causing subsonic vibrations at the predetermined frequency, mild cavitation will occur within the gingival fluid, removing the adherent subgingival plaque 74. The subsonic energy associated with operation of the transducer at approximately 350 cycles per second will additionally damage and demobilize the motile bacteria of nonadherent plaque within the gingival fluid, thereby preventing their attachment to epithelium or tooth surface, and facilitating their removal from the pocket or sulcus by gingival fluid flow. While the vibrating energy level is sufficient to produce subsonic vibrations within the gingual fluid to cause mild cavitation within the fluid to disrupt soft plaque colonies from the surface of the teeth and gingival areas, and to demobilize bacteria, it is insufficient to disrupt or damage the surrounding soft tissues 84.

A second embodiment of the device 90 of the present invention is shown in FIG. 8. The applicator 26 is mounted to the free end 36 of the transducer 24 from a surface 92 of the transducer defined by its length and thickness, and extends generally from the surface. Thus the applicator extends in a direction transverse to the direction of displacement 37 of the transducer as the transducer vibrates.

FIGS. 9 and 10 show a third embodiment of the device 100 of the present invention wherein the handle 22 has a longitudinally extending hood 102 projecting beyond the free end 36 of the transducer 24. The hood 102 encloses the transducer on all but one side from which the applicator 26 extends to protect the inside of the user's cheek and other oral tissue from contacting the vibrating transducer and the vibration of the transducer from being dampened by such contact when positioned inside the mouth during use. A front portion 104 and side portions 106 of the hood shield the end and side surfaces of the transducer. The front and side portions extend outwardly at least coextensive with the bottom face 40 of the transducer when not vibrating. The hood 102 and its front side portions 104 and 106 are each spaced sufficiently apart from the transducer 24 to provide a space 107 therebetween which allows the transducer to vibrate freely without touching the hood.

In FIG. 10, a flexible fluid-exclusion sheath 108 is provided to encapsulate the hood 102 and the transducer 24 to prevent fluid from entering the space 107 therebetween. The sheath is attached to the face 40 of the transducer 24, and the applicator 26 is attached to the sheath in the vicinity of the free end 36 of the transducer to utilize the maximum displacement of the transducer at the free end.

A fourth embodiment of the device 120 is shown in FIG. 11. A second transducer 122 is mounted perpendicularly to the first transducer 24 at the free end 36 thereof and extends generally from the face of the transducer defined by its length and width in the direction of maximum displacement 37 for the first transducer. The second transducer is capable of excitation independent of the first transducer. Thus, the second transducer is capable of vibrating in a direction, indicated by a double-headed arrow 123, generally parallel to the longitudinal axis of the first transducer. The second transducer can be constructed from any number of piezoelectric polymers having resilient characteristics. An insulator 124 is provided between and connects the second transducer to the first transducer to prevent communication of electrical signals from the first transducer to the second transducer. In a variation of the fourth embodiment, the first transducer 24 and the second transducer 122 are electrically connected in parallel. Each transducer is thus excitable by a common driving signal.

Figure 12:
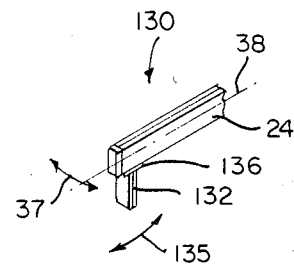
FIG. 12 is a fragmentary isometric view of a second alternative embodiment of the invention providing dual-motion.

A fifth embodiment of the device 130 is illustrated in FIG. 12 using a second transducer 132. The second transducer 132 is mounted perpendicularly to the first transducer 24 at its free end 36 and extends generally from the face of the transducer defined by its length and thickness in the direction perpendicular to the direction of displacement 37 of the first transducer. In this embodiment, the second transducer 132 is also capable of vibrating in a direction, indicated by a double-headed arrow 135, generally parallel to the longitudinal axis of the transducer. An insulator 136 is provided between and connects the second transducer to the first transducer to prevent communication of electrical signals from the first transducer to the second transducer.

Figure 13:
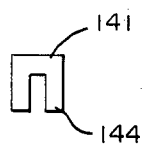
FIGS. 13 through 15 are frontal elevations of various transducer configurations usable with the devices of FIGS. 7, 11 and 12.
Figure 14:
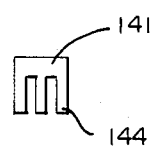
Figure 15:
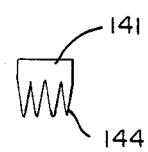

FIG. 7 illustrates a sixth embodiment of the device 140 wherein a plurality of transducers 141 extend generally perpendicularly from an end portion 142 of the handle 22 relative to its longitudial axis. The transducers used with this embodiment and those shown in FIGS. 11 and 12, can assume the various configurations shown in FIGS. 13, 14 and 15. Each of these configurations has a plurality of tapered or pointed fingers 144 to couple sonic energy with the subgingival fluid.

Figure 16:
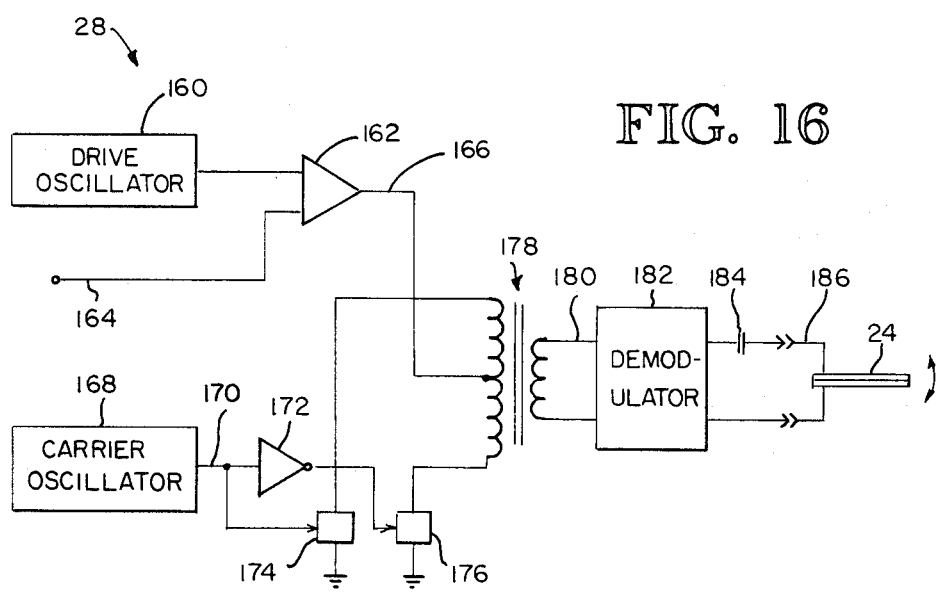
FIG. 16 is a detailed circuit diagram of a second embodiment of the power drive unit of FIG. 1.

FIG. 16 illustrates an electrical schematic diagram for the isolated power drive unit 28. The drive unit has a drive oscillator 160 which generates a sinusoidal signal at the desired transducer operating frequency. A summing amplifier 162 sums the sinusoidal signal from the drive oscillator with a direct-current signal applied to the line 164, resulting in a DC-biased, increased-amplitude, sinusoidal signal on the line 166.

A carrier oscillator 168 generates a high-frequency square wave on the line 170 of a frequency at least five times higher than the desired transducer operating frequency. Further, the frequency of the square wave is sufficiently high enough to prevent physiological stimulation when applied to humans. An inverter 172 inverts the phase of the square wave from the carrier oscillator. A pair of solid-state, high-frequency switches 174 and 176 are provided. The first switch 174 is enabled by the square wave signal from the carrier oscillator 168, and the second switch 176 is enabled by the inverted square wave signal from the inverter 172. Thus, each switch turns on and off at the carrier frequency and acts reciprocally; that is, when the first switch conducts, the second switch does not, and vice versa.

A conventional step-up isolation transformer 178 having a three-tap primary winding and a secondary output winding is provided. Each outermost primary tap is connected through one of the switches to ground. The center primary tap receives the resulting signal on the line 166 from the summing amplifier 162, causing an amplitude-modulated output signal to appear across the secondary output winding of the isolation transformer. The output signal has a carrier frequency at the frequency of the carrier oscillator and an envelope frequency at the frequency of the drive oscillator. For the transducer 24 presently being used, the isolation transformer has a turns ratio suitable for stepping up the amplified sinusoidal signal on the line 166 to an amplitude of approximately 150 volts. Other turns ratios may be substituted to provide sufficient voltage to drive transducers having differing piezoelectric characteristics. The DC-biased, amplified sinusoidal signal on the line 166 is DC-biased so that the solid-state switches 174 and 176 will conduct when enabled by the signal from the carrier oscillator.

A demodulator 182 is provided to receive the amplitude-modulated output signal from the transformer and to recover the sinusoidal signal produced by the drive oscillator 160. The demodulator may consist of a conventional full-wave rectifier with a smoothing capacitor to provide a smooth sinusoidal wave, DC-biased and at the envelope frequency. A capacitor 184 removes the DC bias present in the sinusoidal wave from the demodulator. Thus a rectified sinusoidal signal is presented for transmission to the transducer. This signal has the same frequency as the drive oscillator signal, but the amplitude of its voltage is significantly stepped up. The isolated power drive unit 28 thus provides a relatively low-frequency, sinusoidal signal for the transducer 24 which is isolated from any potential low-frequency, high-current signals which may leak through the isolation transformer 178 if a failure occurs.

In FIG. 4, an alternative embodiment of the power drive unit 200 is shown. The power drive unit has a DC power supply to energize an oscillator and an amplifier. The oscillator produces a sinusoidal signal at the desired operating frequency for the transducer 24. The amplifier amplifies the oscillator signal and introduces the signal to the primary winding of an isolation transformer. The amplifier also serves to buffer the oscillator from the transformer. The isolation transformer has a turns ratio sufficient to step up the amplified sinusoidal signal to drive the transducer from the secondary winding of the transformer. In addition to the power drive units described, batteries, rechargeable or otherwise, can be substituted for the alternating current power sources.

Various other embodiments and variations of the present invention are also contemplated. The scope of the present invention is not to be limited to the above description but is to be defined according to the claims which follow.

We claim:
1. A dental hygiene device comprising:
   an electronically insulated handle of non-conducting material;

an elongated, piezoelectric multimorph transducer having a length substantially greater than the width and a thickness substantially less than the width, said transducer having a first end portion rigidly attached to the handle for cantilever mounting thereto, an unattached second end portion which is free to vibrate with maximum displacement substantially at the transducer's resonant frequency and substantially transverse to the transducer length, and an unrestrained mid-portion extending outwardly from the handle and between the attached first end portion and the unattached second end portion, the transducer being bendable in response to an electrical signal for generating relatively low-energy vibrations of a predetermined frequency to disrupt and remove plaque and to interrupt and limit the process of plaque maturation and development;

means for transmitting electrical signals to the transducer; and at least one applicator member fixed to the free second end portion of the transducer and extending therefrom for scrubbing exposed surfaces and for transmitting the vibrations to the gingival areas, the transducer being operable to cause mild cavitation within the subgingival fluid to disrupt plaque colonies and to demobilize motile bacteria without harming the surrounding soft tissue.

2. The device of claim 1, further including means for generating a high-voltage, low-frequency signal for transmission to the transducer to drive the transducer at its resonant frequency or multiples thereof.

3. The device of claim 2 wherein the signal generating means drives the transducer with sufficient vibratory energy to produce vibrations within the gingival fluid to cause mild cavitation within the fluid to disrupt soft plaque colonies from the surface of the teeth and gingival areas, and to demobilize motile bacteria, but with insufficient energy to damage the soft tissue.

4. The device of claim 3 wherein the transducer has a size and mass to resonate at the predetermined frequency, and the predetermined frequency is in a substantially sub-audio range.

5. The device of claim 4 wherein said transducer is electrically insulated by a covering protecting the user from electrical shock.

6. The device of claim 3 wherein the signal generating means is an isolated power drive unit to isolate the transducer from low-frequency, high-current signals, comprising:

a drive oscillator to generate a sinusoidal signal at the predetermined frequency for the transducer;

a summing amplifier for summing the sinusoidal signal from the drive oscillator with a direct current signal and for amplifying the resulting signal;

a carrier oscillator to generate a square wave signal of sufficiently high frequency to prevent physiological stimulation;

an inverter to invert the phase of the square wave signal from the carrier oscillator;

a pair of solid-state, high-frequency switches, the first switch enabled by the signal from the carrier oscillator and the second switch enabled by the inverted square wave signal from the inverter so that each switch turns on and off at the carrier frequency, wherein the switches act reciprocally, that is, when one switch conducts, the other does not;

a step-up isolation transformer having a three-tap primary winding and an output winding, wherein each outermost primary tap is connected through one of the switches to ground and wherein the center primary tap receives the resulting signal from the summing amplifier, causing an amplitude-modulated output signal to appear across the output winding, having a carrier frequency at the frequency of the carrier oscillator and an envelope frequency at the drive oscillator frequency, and also having a turns ratio sufficient to substantially step up the voltage of the signal across the primary winding;

a demodulator to receive the amplitude-modulated output signal from the output winding of the transformer and to recover the sinusoidal signal from the drive oscillator; and a capacitor to remove any direct-current bias from the output of the demodulator.

7. The device of claim 1 wherein the transducer has at least two layers of piezoelectric material of differing polarity bonded to an intermediate conductive layer and means for application of an electrical signal to an opposed unbonded surface of each of the piezoelectric layers and wherein the dimensions of the transducer are chosen such that the transducer resonates at the predetermined frequency when a time-varying electric signal is applied to the opposed unbonded surfaces of the piezoelectric layers.

8. The device of claim 7, including means for application of an electrical signal to the intermediate conductive layer.

9. The device of claim 1 wherein the transducer is selectively detachable from the handle.

10. The device of claim 1 wherein the applicator is a brush having a plurality of bristles sized to enter subgingival crevices and pockets and to enter fluid proximal to the pockets to transmit vibratory energy to the pockets.

11. The device of claim 1 wherein the applicator is attached to and extends generally outward from a surface of the transducer defined by the length and width of the transducer for vibration generally in the direction of extension of the applicator.

12. The device of claim 1 wherein the applicator is attached to and extends generally outward from a surface of the transducer defined by the length and thickness of the transducer for vibration generally in the direction transverse to the direction of extension of the applicator.

13. The device of claim 1 wherein the handle has a clamping portion to fix the first end portion of the transducer at a nodal point for its resonant frequency, inward from the first end and a cavity within the handle adjacent to the clamping portion into which the first end portion extends, to allow the first end of the transducer within the cavity to vibrate freely, minimizing vibration of the handle.

14. A dental hygiene device comprising:

an electronically insulated handle of non-conducting material;

an elongated, piezoelectric multimorph transducer having a length substantially greater than the width and a thickness substantially less than the width, said transducer having a first end portion rigidly attached to the handle and an unattached second end portion which is free to vibrate with maximum displacement substantially at the transducer's resonant frequency, the transducer being bendable in response to an electrical signal for generating relatively low-energy vibrations of a predetermined frequency to disrupt and remove plaque and to interrupt and limit the process of plaque maturation and development, the transducer having at least one unbonded piezoelectric surface with a substantially coextensive spring bonded thereto to alter the natural resonant frequency of the transducer;

means for transmitting electrical signals to the transducer; and at least one applicator member fixed to the second free end portion of the transducer and extending therefrom for scrubbing exposed surfaces and for transmitting the vibrations to the gingival areas, the transducer being operatable to cause mild cavitation within the subgingival fluid to disrupt plaque colonies and to demobilize motile bacteria without harming the surrounding soft tissue.

15. A dental hygiene device comprising:

an electronically insulated handle of non-conducting material;

an elongated, piezoelectric multipmorph first transducer having a length substantially greater than the width and a thickness substantially less than the width, said first transducer having a first end portion rigidly attached to the handle and an unattached second end portion which is free to vibrate with maximum displacement substantially at the first transducer's resonant frequency, the first transducer being bendable in response to an electrical signal for generating relatively low-energy vibrations of a predetermined frequency to disrupt and remove plaque and to interrupt and limit the process of plaque maturation and development;

means for transmitting electrical signals to the first transducer;

at least one applicator member fixed to the second free end portion of the first transducer and extending therefrom for scrubbing exposed surfaces and for transmitting the vibrations to the gingival areas, the first transducer being operatable to cause mild cavitation within the subgingival fluid to disrupt plaque colonies and to demobilize motile bacteria without harming the surrounding soft tissue, the applicator being a second piezoelectric multimorph transducer bendable in response to an electrical signal and positioned for vibration in a direction generally parallel to the longitudinal direction of the first transducer; and means for transmitting electrical signals to the second transducer.

16. A dental hygiene device comprising:

an electronically insulated handle of non-conducting material;

an elongated, piezoelectric multimorph transducer having a length substantially greater than its width and a thickness substantially less than its width, said transducer having a first end portion rigidly attached to the handle for cantilever mounting thereto, an unattached second end portion which is free to vibrate substantially transverse to the transducer length, and an unrestrained mid-portion extending between the attached first end portion and the unattached second end portion, the transducer being bendable in response to an electrical signal for generating relatively low-energy vibrations of a predetermined frequency to cause mild cavitation of gingival fluid to disrupt and remove plaque and to demobilize motile bacteria;

means for transmitting electrical signals to the transducer to cause said transducer to resonate at the predetermined frequency;

an applicator attached to, and extending generally outward from the free second end portion of the transducer for transmitting the vibration of the transducer to the gingival fluid; and a protective hood at least longitudinally coextensive with the transducer and spaced sufficiently apart therefrom to allow the transducer to vibrate freely, the hood having an open side through which the applicator extends.

17. A dental hygiene device comprising:

an electronically insulated handle of non-conducting material;

an elongated, piezoelectric multimorph transducer having a length substantially greater than its width and a thickness substantially less than its width, said transducer having a first end portion rigidly attached to the handle and an unattached second end portion which is free to vibrate, the transducer being bendable in response to an electrical signal for generating relatively low-energy vibrations of a predetermined frequency to cause mild cavitation of gingival fluid to disrupt and remove plaque and to demobilize motile bacteria;

means for transmitting electrical signals to the transducer to cause said transducer to resonate at the predetermined frequency;

an applicator attached extending generally outward from the free second end portion of the transducer for transmitting the vibration of the transducer to the gingival fluid;

a protective hood at least longitudinally coextensive with the transducer and spaced sufficiently apart therefrom to allow the transducer to vibrate freely, the hood having an open side; and a fluid exclusion sheath surrounding the hood and the transducer to prevent fluid from entering a space therebetween, the sheath being bonded to the transducer at the free second end portion to communicate vibrations from the transducer to the sheath, the applicator being attached to an outward side of the sheath proximal to the free second end portion of the transducer.

18. The device of claim 17 wherein the protective hood has a front portion and side portions extending generally around the transducer and spaced sufficiently therefrom to allow the transducer to vibrate freely.

19. A dental hygiene device comprising:

an electrically insulated handle of nonconducting material;

at least one elongated piezoelectric multimorph transducer having a length substantially greater than its width and thickness substantially less than its width, wherein the transducer is constructed from a resilient polymer, the transducer having a first end portion rigidly attached to the handle for cantilever mounting thereto at a transducer nodal point and extending therefrom generally perpendicular to the longitudinal axis of the handle, and having an unattached second end portion extending from the handle, which is free to vibrate in a direction substantially transverse to the transducer length at an anti-nodal point and oriented to engage the gingival areas, wherein the second end portion has at least one pointed portion being sufficiently narrow to enter subgingival crevices and pockets and enter fluid proximal therewith to transmit vibratory energy thereto and an unrestrained midportion extending outwardly from the handle and between the attached first end portion and the unattached second end portion, the transducer being bendable in response to an electrical signal for generating relatively low-energy vibrations of a predetermined resonant frequency to cause mild cavitation in gingival fluid to disrupt and remove plaque and to demobilize motile bacteria for interrupting and limiting the process of plaque development and maturation; and means for transmitting electrical signals to the transducer to cause the transducer to vibrate at the predetermined resonant frequency or multiples thereof.

* * * * *